United States Patent [19]

Consalvo

[11] 4,098,275

[45] Jul. 4, 1978

[54] DUAL FLOW CANNULA SET

[76] Inventor: Dante Vincent Consalvo, Everett, Mass.

[21] Appl. No.: 752,274

[22] Filed: Dec. 20, 1976

Related U.S. Application Data

[63] Continuation-in-part of Ser. No. 636,067, Nov. 28, 1975, abandoned.

[51] Int. Cl.² ............................................. A61M 1/03
[52] U.S. Cl. ............................... 128/214 R; 128/221; 128/DIG. 3
[58] Field of Search ............ 128/214 R, 214 B, 214.2, 128/214.4, 221, DIG. 3, DIG. 16, 347; 222/80–81; 141/329

[56] References Cited

U.S. PATENT DOCUMENTS

| 1,290,647 | 1/1919 | Nyvall | 128/214 R X |
| 2,137,132 | 11/1938 | Cooley | 128/214.2 X |
| 2,409,343 | 10/1946 | Curtis | 128/214.2 |
| 2,474,665 | 6/1949 | Guarino | 128/DIG. 3 |
| 2,625,932 | 1/1953 | Salisburg | 128/214.2 |

Primary Examiner—Dalton L. Truluck
Attorney, Agent, or Firm—Russell & Nields

[57] ABSTRACT

A dual cannula having two adjoining tubes, a leader tube and a follower tube, in staggered arrangement so as to form two separate and distinct passageways for the withdrawal and return of blood to a body. The blood return passageway terminates with a needle aperture and the blood withdrawal passageway has a sheltered aperture. The outer dimensions of the needle portion of the leader tube are substantially the same as the total outer dimensions of the two adjoining tubes for the distance which the cannula is adapted to be inserted into a body, whereby the sheltered aperture is sheltered by the needle portion of the leader tube. Means are provided for shielding the sheltered aperture.

5 Claims, 9 Drawing Figures

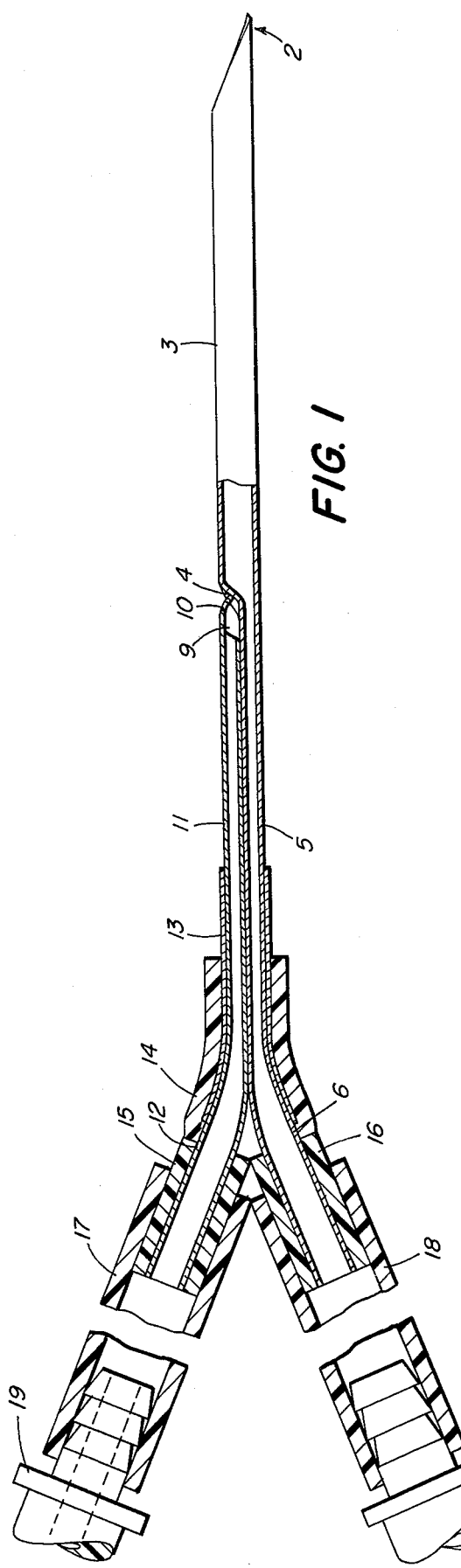
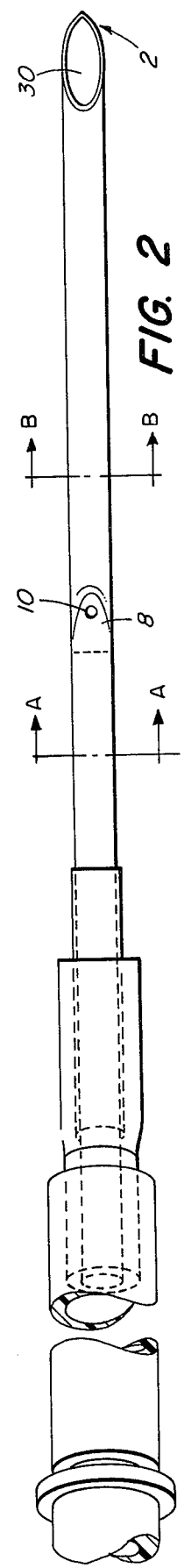
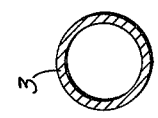
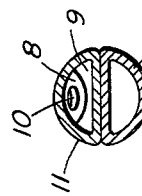
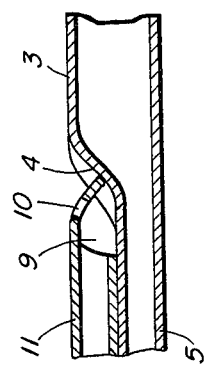
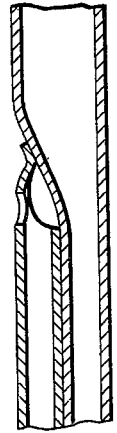

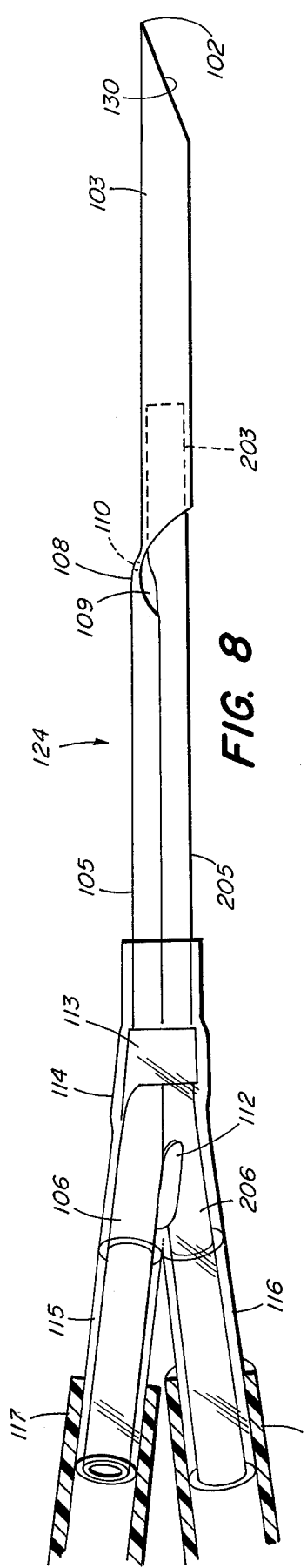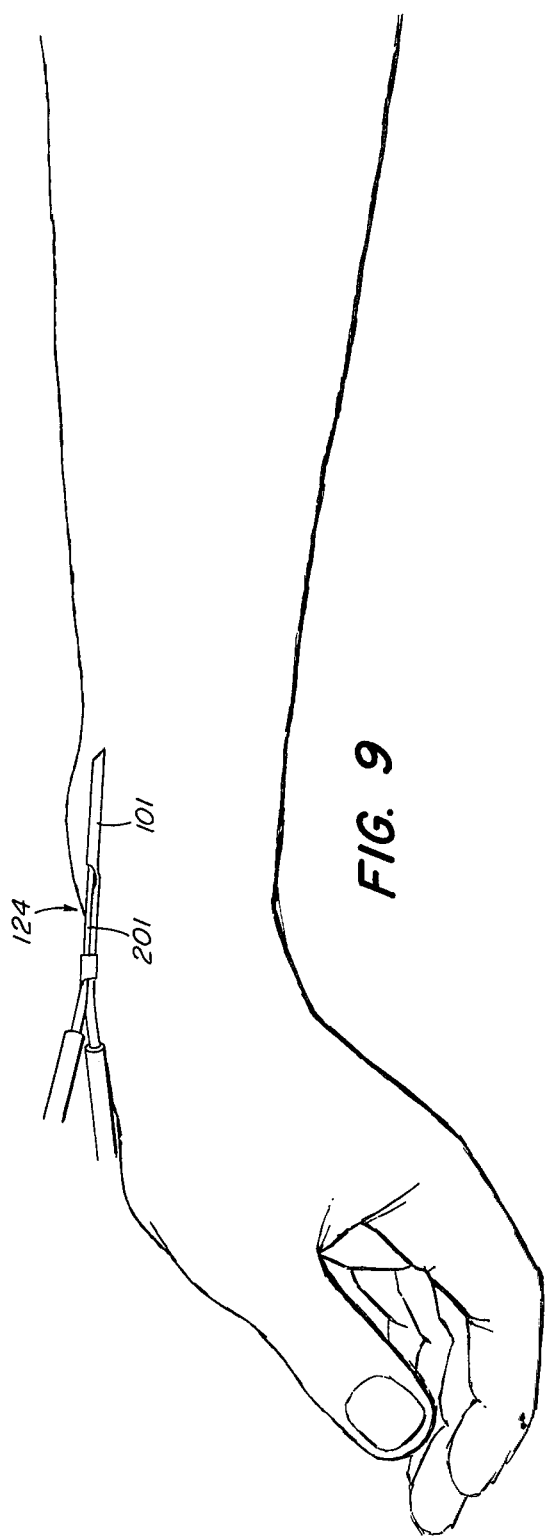

DUAL FLOW CANNULA SET

REFERENCE TO RELATED APPLICATION

This application is a Continuation-In-Part of application Ser. No. 636,067 filed Nov. 28, 1975 for "DUAL FLOW CANNULA SET" which application has been expressly abandoned under Rule 138.

BACKGROUND OF THE INVENTION

The field of the present invention is surgical cannulas used to support the flow of blood, as in a hemodialysis. In particular, the present invention relates to surgical cannulas adapted simultaneously to withdraw and return blood through a single cannula, thereby permitting a single venipuncture.

The duplex needle of U.S. Pat. No. 2,137,132 has a dual tubular construction, but the two tubes merge within the needle. Blood cannot be withdrawn through one tube and returned through the second tube of the same needle. Instead, the treatment of blood in U.S. Pat. No. 2,137,132 requires two separate needles. The fluid inlet-outlet device of Curtis U.S. Pat. No. 2,409,343 also does not disclose a suitable method for withdrawing and returning blood to a body. Instead, it is designed "for piercing self-sealing insertion through a puncturable closure of a container," and does not disclose means for overcoming the problems associated with the withdrawal of blood from a blood vessel. In the case of the Curtis device the rigid walls of the container will not collapse during withdrawal of the fluid, and there is no danger of blockage of the intake opening. On the other hand, in the case of a cannula inserted into a blood vessel, the walls of the blood vessel collapse and tend to block the intake opening. The Curtis patent teaches that an intake opening be as open as possible, with preferably nothing to interfere with the withdrawal of fluid. The Curtis device would not, therefore, be an acceptable means for the withdrawal of blood from a blood vessel due to the collapsible nature of the blood vessel walls. Additionally, the Curtis device is not suitable for insertion into a human or other animal body due to the danger of multiple punctures resulting from exposed tips of the two side-by-side tubes.

The prior art reveals several methods by which blood can be withdrawn and returned to the body. First, the blood can be withdrawn from an artery and returned to the vein by means of two separate surgical implantations. This external by-pass is called a shunt. The second method of blood withdrawal involves a fistula. The fistula method entails an internal surgical connection between an artery and a vein. Because of the higher blood pressure in an artery, the vein will expand below the point of connection. This area of expansion has the appearance of a blood bubble, and will be referred to as the fistula. The fistula method calls for an intake needle to be inserted into the fistula against the flow of blood. In dual venipuncture devices a second needle (the outflow needle) is then inserted into a different vein downstream, and placed in the same direction as the flow of blood. In the second of the above methods, two separate needles are used, requiring two separate punctures.

The prior art discloses various methods for single needle dialysis. Examples may be found in U.S. Pat. Nos. 3,756,234 and 3,830,234, which discuss in general terms only a hollow cannula where the separation of arterial and venous branches is done via a T-joint and valves. These valves alternately open and close with pressure build-up, resulting in time separated pulses between the arterial and venous branches.

SUMMARY OF THE INVENTION

The present invention comprehends a cannula comprising an intake passageway and a separate and distinct outflow passageway. The intake passageway aperture is partially shielded to prevent blockage by the blood vessel and to provide a substantially continuous smooth external surface to the blood vessel.

In both embodiments of the present invention the structural members include a first tube and a second tube, both usually of metallic construction, and suitable tubing. Each tube has a forward end and a rear end, and the tubing is connected between the rear ends of the two tubes.

In the preferred embodiment of the present invention the first tube is provided with a lateral aperture which serves two functions. The first function is as the aperture to the intake passageway, which is formed by the first tube. The second function is as an aperture through which the formed end of the second tube may be inserted, facing toward, but not projecting beyond, the forward end of the first tube. The forward end of the second tube is thus completely sheathed in the first tube. The second tube forms the outflow passageway, but it "borrows" the forward end of the first tube and uses it in conjunction with its own forward end. The aperture to the intake passageway is now shielded not only by the wall of the first tube itself, which extends continuously and integrally over the aperture, but also by the second tube at a position adjacent to that at which the forward end of the second tube is snugly embraced by the first tube. This provides a shield for the aperture which has a smooth external surface.

A second embodiment of the present invention comprehends a cannula comprising two externally adjoining tubes of unequal length and in a staggered arrangement, so that the shorter tube is nestled against and sheltered by the longer tube, each tube being capable of transporting fluids to and from the body, said arrangement being such as to form a single needle for insertion into the body.

The present invention therefore relates to an improved cannula of the type in which only a single needle is used to withdraw and return blood to the body along separate and distinct passageways without mixing. The improved cannula of the invention has no moving parts and has favorable flow pressure characteristics. The needle is placed inside a fistula in the direction of the blood flow, and blood is withdrawn through the arterial tube by suction created by a pump. After treatment of the blood, it is returned to the body through the venous tube downstream from the intake of the arterial tube.

Some prior art methods of single needle dialysis employed needles having the disadvantage that the treated and untreated blood alternatively flowed through the same passageway. The present invention keeps the passageways for the withdrawn blood and returned blood separate at all times while inside the cannula, and does no without moving parts which might wear out or jam.

An essential feature of the present invention is the shielding means in the vicinity of the cannula aperture of the blood-intake (or arterial) tube. When blood is withdrawn through a tube which is placed inside a narrow blood vessel, the walls of that blood vessel tend to collapse and block the opening of that tube, but the shielding means of the invention prevents the walls of the blood vessel from blocking the arterial tube cannula aperture and thus leaves enough space for effective withdrawal of blood.

The shape of the two tubes conducting the flow of blood is also important. First, for the distance that the two passageways are side-by-side, each tube has a semi-circular interior cross-sectional area. With this construction the total fluid flow resistance will be lower than in the case of two cylindrical tubes inside a cylindrical tube of the same diameter as the overall external diameter of the two adjoining semi-cylindrical sections. This reduced resistance is due to the increased internal cross-sectional area through which fluid can flow. The total fluid flow resistance will also be lower in the present invention than in the case of two tubes one inside the other, as in U.S. Pat. No. 2,137,132. This is true if, in the latter situation, the outside tube has a diameter equal to the overall external diameter of the two adjoining semi-cylindrical sections of the present invention. This reduced resistance is due to the decreased surface contact between the fluid and the tubes. Secondly, the venous and arterial tubes are shaped and assembled in a manner which provides a smooth transition from the front needle portion of the venous tube to the intermediate region of the cannula where the two semi-cylindrical portions adjoin.

BRIEF DESCRIPTION OF THE DRAWINGS

FIG. 1 is a side view partly in section of one embodiment of the cannula of the invention in a horizontal position;

FIG. 2 is a top view of the cannula of FIG. 1;

FIG. 3 is a sectional view of the shielding means of the arterial tube bonded or welded to the venous tube;

FIG. 4 is an enlarged sectional view of the shielding means of the arterial tube and the dimple area of FIG. 1;

FIG. 5 is a cross-sectional view along line A—A of FIG. 2;

FIG. 6 is a cross-sectional view along line B—B of FIG. 2;

FIG. 8 is a side view partly in section of a preferred embodiment of the cannula of the invention in a horizontal position, and FIG. 9 is a view showing the embodiment of FIG. 8 inserted into a human arm.

DESCRIPTION OF THE PREFERRED EMBODIMENTS

Figure 7:
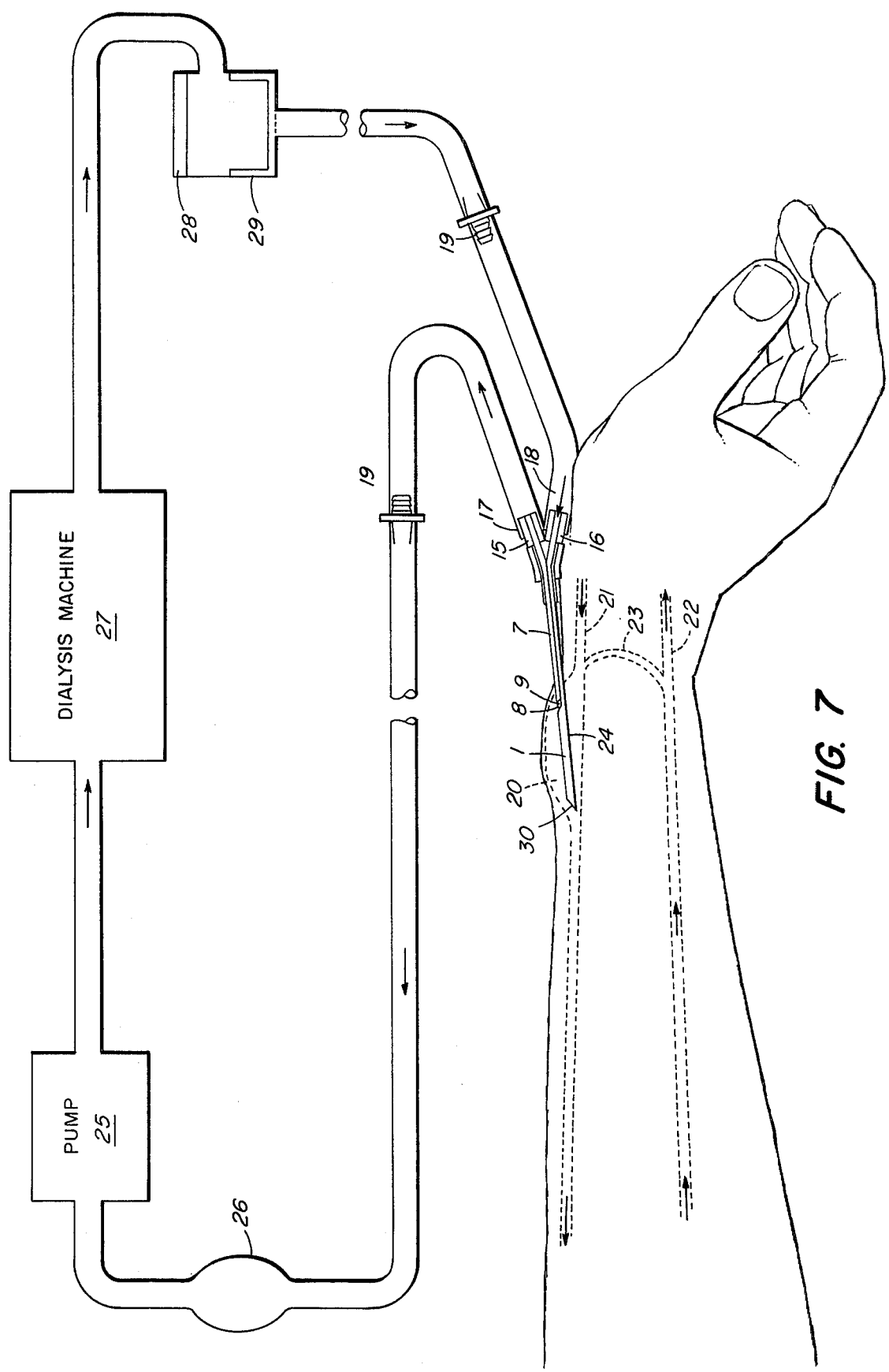
FIG. 7 is a view of one embodiment of the cannula of the invention in operation.

In reference to FIGS. 1 through 7, the cannula therein shown comprises a needle-shaped venous tube 1 and a shorter arterial tube 7 held together to form a "Y" shaped cannula. The venous tube 1 has a front end with a cannula aperture 30 cut at an angle and coming to a sharp point 2, to permit easy puncture of the skin and blood vessel. The point 2 is located opposite to the side of the venous tube which adjoins the arterial tube 7. Thus, when the cannula is being inserted into a body, the protective flap 8 at the front of the arterial tube will tend to push towards the dimple 4 of the venous tube, thereby insuring that the arterial tube 7 will follow the venous tube 1 into the same blood vessel without making a second puncture. The dimple 4, and the location of the tip of the flap 8 therein, insures that the tip of the flap 8 cannot stick out and cause injury. The needle portion 3 of the venous tube has a circular exterior cross-sectional area, extending back to the dimple 4 where the arterial tube is held adjacent to the venous tube. The intermediate region 5 of the venous tube where the two tubes are held adjacent has a semi-circular cross-sectional area, with the result that the total external cross-sectional area of the two adjacent tubes (FIG. 5) is approximately equal to the external cross-sectional area of the needle portion 3 of the venous tube (FIG. 6). The rear portion or coupling end 6 of the venous tube, having a circular cross-sectional area approximately equal to that of its needle portion 3, may be bent away from the rear portion or coupling end 12 of the arterial tube to form the shape of a "Y".

The arterial tube 7 has a front end with shielding means in the form of a rigid flap 8 which protects and partially covers the arterial tube cannula aperture 9. The shielding means may also be in the form of a tongue, finger, or leaf. The flap 8 commences as a continuation of a portion of the circumference of the arterial tube 7, but then bends towards the venous tube 1 and, as it does so, the width thereof is narrowed so as to form a triangle whose apex is adapted to engage the dimple 4. A hole 10 is provided in the flap 8 to permit additional fluid intake. In looking at the cannula extending horizontally with the venous tube 1 lowermost, the flap 8 extends in a substantially horizontal direction from the top portion of the arterial tube 7, and then curves downwards until it contacts the dimple 4 in the outside of the venous tube 1. The result is a space 9 on each side of the flap 8 through which fluid may flow. The intermediate region 11 of the arterial tube 7 has the same semi-circular cross-sectional area as that of the venous tube 1 for the distance that the two tubes are adjoining.

The two metal tubes 1,7 which comprise the cannula are constructed in the following manner. First, the desired internal semi-circular cross-sectional area of the intermediate region 5,11 of each tube is computed. The dimensions of the cannula have maximum and minimum constraints. The cannula must not exceed a diameter suitable for a single venipuncture, thereby fixing the maximum permissible external dimension across the intermediate regions 5, 11. Furthermore, the cannula must be of sufficient size to support the flow of blood in a hemodialysis (for example, 300 to 350 cc/min is a typical range), thereby fixing the minimum permissible internal cross-sectional area of each tube 1,7. Within this range of dimensions, a tube is chosen having an internal cross-sectional area greater than the minimum necessary, and having an external cross-sectional no more than half the maximum allowed for a single tube cannula. These requirements are met by a 15 guage (0.072 in. O.D.) thin wall (0.005 in.) stainless steel tube. Second, the enlarged inside diameter sections 3, 6, 12 of both tubes are obtained by driving a hardened steel pin with the desired diameter through the core of each thin tube. This second step is performed by placing each tube in a suitable fixture in a vise. The bottom portion of this fixture has a semi-cylindrical groove in which the tube to be enlarged can lie. The radius of the rear portion of this groove is equal to one-half the outside diameter of the pre-enlarged tube. The radius of the front portion of this groove will be larger to allow for the enlargement of the tube. This larger front portion of the groove extends for the distance which the tube is to be enlarged. The top portion of this fixture has the same shape as the bottom portion. Thus, when the tube is placed between the top and bottom portions of the fixture and clamped in a vise, the tube will be held securely while permitting enlargement over the desired distance. The end of the tube to be enlarged is flared to the desired outside diameter by driving a hardened steel pin with a conical end into the open end of the tube. After formation of the flared end, the flaring pin is withdrawn and another hardened steel pin with the desired diameter is driven by means of a hammer through the core of the tube for the desired distance to be enlarged.

Thus, in making the venous tube 1, the 15-guage stainless steel tube is placed in the fixture and clamped in a vise, with a sufficient length of tube in the large groove portion of the fixture to form the needle portion 3. The needle portion 3 of the venous tube is formed by first flaring the end, and then by driving the hardened steel enlarging pin by means of a hammer through the core of the tube for the desired length of the needle portion 3. After withdrawal of the enlarging pin, the tube is removed from and returned to the fixture and clamped in a vise such that only the coupling end 6 is in the large groove portion of the fixture. The coupling end 6 of the venous tube is formed by first flaring the end, and then by driving the hardened steel enlarging pin through the core of the tube for the desired length of the coupling end 6. The enlarging pin is then withdrawn. In making the arterial tube 7, the 15-guage stainless steel tube is also placed in the fixture and clamped in a vise, and the coupling end 12 formed by the same method as the coupling end 6 of the venous tube. This method is preferred over the reverse method whereby a tube of larger diameter is drawn into a tube of smaller diameter. In the latter method, the smooth internal surface of the tube is usually destroyed.

In order to have a smooth internal and external transition between the small and large diameter portions of the two tubes, a special tool is inserted through the wide diameter end. The front portion of this tool has a semi-circular cross-sectional area which fits inside the narrow portion of the tube. The rear portion of the tool has a circular cross-sectional area which fits inside the enlarged portion of the tube. In addition, one edge of the tool is straight, while the opposite edge has a 45-degree slope at the transition between the semi-cylindrical and cylindrical portions. With the tool inside the tube, external pressure is applied along one edge of the small diameter portion of the tube. This pressure is applied in the following manner. With the tube on a horizontal surface in a groove of radius equal to one-half the outside diameter of the large portion of the tube, the flat edge of the front semi-cylindrical portion of the tool is placed upwards inside the tube. The straight edge of the tool will thus be facing downwards. Force is then applied by a hand-held block on the top surface of the small diameter portion (which will become the intermediate region 5 or 11) of the tube. This block has a flat bottom surface, with an angle of approximately 45° at one edge and approximately 30° at the other edge of the bottom surface. This shape provides a relatively smooth transition from the small and large diameter portions of the two tubes. Upon application of pressure, the small portion of the tube yields and conforms to the straight edge of the inside tool, and also becomes semi-circular in shape. The internal tool is then removed. This method is repeated to obtain a smooth edge between the front portion 3 and the intermediate region 5 of the venous tube, between the intermediate region 5 and the coupling end 6 of the venous tube, and between the intermediate region 11 and the coupling end 12 of the arterial tube.

The dimple 4 in the venous tube 1 is formed by similar means, i.e., a preformed tool is inserted into the venous tube 1, whereby external pressure on the tube will cause a dimple of a size permitted by the internal tool to form. The front portion of the dimple tool is narrow and semi-cylindrical and fits inside the intermediate region 5 of the venous tube 1. The rear portion of this tool has a wider diameter, and a 45-degree slope between the front and rear portions. Thus, when the dimple tool is inserted through the needle portion 3 of the venous tube, it will fit snugly inside the venous tube 1. The dimple tool also has a cavity at the slanted edge between the forward and rear portions. The size of this cavity determines the size of the dimple 4 to be formed. The venous tube 1 with the inserted dimple tool is placed on a horizontal surface with a groove of radius equal to one-half of the diameter of the large portion of the tube. The tube is placed with the flat portion of the intermediate region 5 facing upwards. Force is then applied by tapping a hardened steel pin with a rounded end against the slanted edge between the needle portion 3 and the intermediate region 5 of the venous tube. After formation of the dimple 4, the tool is removed.

At this time, the coupling ends 6, 12 of the two tubes are bent by hand into the desired "Y" shaped position. In order to have the bend occur at the transition between the narrow intermediate regions 5, 11 and the wider couplings ends 6, 12 and not along the intermediate regions 5, 11 where the venous and arterial tubes adjoin, the following bending procedure is used. The tube is placed in a fixture whose bottom portion has a groove and a rounded grooved corner. The top fixture is also grooved. The groove in both portions of the fixture is of a sufficient radius to hold the tube securely when the fixture is clamped in a vise. The coupling end 6, 12 of the tube extends over the rounded end of the fixture and is not held by the fixture. The coupling end 6, 12 is then bent by hand around the rounded grooved corner of the bottom portion of the fixture.

After the bending operation, the two tubes 1, 7 are cleaned by ultrasonic means. The point 2 of the needle portion 3 of the venous tube can be made by cutting one end of the venous tube (having a wide diameter section on both sides of the intermediate region 5) at such an angle that the point 2 extends from the straight edge of the tube. The preferred distance between the venous tube outflow cannula aperature 30 and the arterial tube intake cannula aperture 9 is 1.1 inches, and a suitable range is between 1.0 and 1.2 inches. After the point 2 is cut, the venous tube 1 is ultrasonically cleaned again.

The two tubes forming the single needle are held together by the following means. First, medical grade adhesive silicone is applied to the flat edge of the intermediate region 11 of the arterial tube 7. The adhesive is applied to the arterial tube 7, rather than the venous tube 1, to prevent accidental blockage of the intake openings 9, 10. The silicone adhesive also serves as a seal, to prevent blood from seeping out of the vein between the two tubes 1, 7. By means of this seal and the pressure of the surrounding flesh tissue, all blood leaving the fistula 20 is transported through the arterial tube 7 without loss. The two tubes 1, 7 are then brought into contact along the intermediate regions 5,11 in such a manner that the end of the curved flap 8 fits into the dimple 4. Second, a cylindrical stainless steel sleeve 13 with a "Y" shaped flared end is slid with the flared end first, over the front of the venous tube 1 and then around both tubes 1, 7 to the point where the two tubes diverge to form the "Y" shape. This step accomplishes a function in addition to holding the two tubes firmly together. As the metal sleeves 13 is pushed back around the two tubes, it picks up the excess silicone adhesive some of which is applied to the end of the sleeve and the rest discarded. With the sleeve 13 in place, the adhesive is given a curing time of at least 24 hours. Third, a sleeve of Tygon tubing 14 is slid over the front of the venous tube 1 and over the stainless steel sleeve 13. This step is facilitated by applying "Tygon Bond" (a ketone solvent) to the inside of the Tygon tubing. Finally, two sections of Tygon tubing 15, 16 are slid over the coupling ends 6, 12 of the arterial and venous tubes respectively, again facliated by applying "Tygon Bond" to the inside of the Tygon tubing. These two supply end Tygon tubes 15, 16 abut against each other and the Tygon sleeve 14. These areas of intersection are then coated with "Tygon Bond", which chemically reacts with the Tygon tubing so that the three sections of tubing 14, 15, 16 become bonded together. At this time a section of Tygon tubing 17, 18 is cemented by means of "Tygon Bond" to the two supply end Tygon tubes 15, 16 respectively.

Referring to FIGS. 8 and 9, therein is shown a preferred embodiment of the cannula of the present invention. The dual flow cannula 124 comprises a leader tube 101 and a follower tube 201 so arranged to provide two separate and distinct passageways for the treatment of blood with only a single venipuncture.

The leader tube 101 comprises a forward portion 103, a shield segment 108, an intermediate portion 105, and a coupling end 106. The forward leader portion 103 has a cannula aperture 130 and terminates at an angle coming to a sharp point 102. Furthermore, this forward leader portion 103 has a circular cross-sectional area sufficiently large to snugly accommodate the forward portion 203 of the follower tube discussed below. The intermediate leader region 105, the forward leader portion 103, and the shield segment 108 form a structurally continuous member, and constitutes one piece. Located along the shield segment 108 is a hole 110 to allow for additional blood withdrawal.

The function of the shield segment 108 in the embodiment of FIG. 8 is similar to the flap 8 of the embodiment of FIG. 1. As mentioned above, the shield segment 108 permits effective withdrawal of blood while preventing the occlusion, by blood vessel walls, of the intake opening 109 of the blood withdrawal passageway formed by the intermediate portion 105 and coupling end 106 of the leader tube. Furthermore, the shield segment 108 provides a smooth transition past the intake opening 109 from the intermediate leader portion 105 to the forward leader portion 103, in order to avoid any puncture of the body other than that produced by the sharp point 102.

Despite the above-mentioned similarities between the flap 8 of the first embodiment shown in FIG. 1 and the shield segment 108 of the embodiment shown in FIG. 8, there are significant differences. First, the shield segment 108 of FIG. 8 is integral with the forward 103 and intermediate 105 portions of the leader tube 101, i.e., the tube causing the puncture as the cannula is inserted into a body. The flap 8 shown in FIGS. 1 and 2, however, is integral with the arterial tube 7 through which blood is withdrawn, said flap extending to and contacting the exterior of the venous tube 1, the blood-return tube. The structural differences between the shield segment 108 and the flap 8 has important consequences. In the embodiment of FIG. 1, in which is shown two tubes 1, 7 in a side-by-side staggered arrangement, it is vital that the flap 8 of the arterial tube 7 make a firm contact with the venous tube 1, and that this contact be maintained while the cannula is inserted into a body, to avoid the danger of a second tip causing additional hazardous punctures. This firm contact is essential because the two tubes 1, 7 tend to be forced apart as the cannula 24 is being inserted into a body and also while the cannula 24 is partly within a body. To minimize the force of separation during insertion of the cannula 24, the point 2 of the cannula 24, as shown in FIG. 1, is placed laterally remote from the flap 8. With the point 2 on the bottom as the cannula 24 is inserted in a slightly downward angle into a body, as shown in FIG. 7, the flap 8 of the arterial tube 7 lying on top of the venous tube 1 will tend to be pushed towards, rather than away from, the exterior surface of the needle portion 3 of the venous tube. Aside from the relative positions of the point 2 and the flap 8, the arterial tube 7 and venous tube 1 are also held together by medical grade adhesive silicone, as well as a combination of metal sleeve 13 and Tygon tubing 14, 15, 16 as already discussed above.

In the embodiment of FIG. 8, however, the forces of separation placed upon the two tubes 101, 201 as the cannula 124 is being inserted into a body and also while within a body are not applied at the shield segment 108. As shown in FIGS. 8 and 9, the point 102 of the cannula 124 is placed on the same side as the shield segment 108. Furthermore, the shield segment 108 is integral with the leader tube 101, and there is no second point which could separate to cause additional punctures beyond that produced by the sharp point 102. As mentioned in more detail below, the forward portion 203 of the follower tube is, in effect, sheathed within the forward portion 103 of the leader tube. Consequently, with the point 102 lowermost, as the cannula 124 is inserted in a slightly downward direction as shown in FIG. 9, the forces of separation act upon the forward follower portion 203 within the forward leader portion, as well as upon the other means for holding the two tubes 101, 201 together, such means including medical grade adhesive silicone, sleeve 113, and Tygon tubing 114, 115, 116 all discussed more fully below. With the shield segment 108 integral with the forward leader portion 103 and intermediate leader portion 105, the result is a very secure combination of the two tubes 101, 201, the latter partly inside the former, with virtually no risk of any separation during normal use of the cannula 124. In this last described embodiment, the cannula 124 is inserted with its point 102 lowermost, and the intake aperture 109 is also lowermost. One advantage of this construction is that gravity assists in keeping the blood vessel walls away from the intake opening 109 and hole 110. Although FIGS. 8 and 9 depict the channel 124 with its forward point 102 on the same side as the shield segment 108, it is to be understood that the cannula 124 may instead be constructed with the point 102 at any desired position at the end of the forward leader portion 103.

As discussed above, the shield segment 108 integrally connects the forward leader portion 103 with the intermediate leader region 105. This intermediate leader region 105 is similar in design to the intermediate region 11 of the arterial tube 7 of the embodiment of FIG. 1, with a semi-circular cross-sectional area. Additionally, the coupling end 106 of the leader tube is similar to the coupling end 12 of the arterial tube 7.

Having thus described the leader tube 101, the follower tube 201 construction will now be set forth, followed by a description of how the two tubes are assembled into an embodiment of the dual flow cannula of the present invention.

The follower tube 201 comprises a forward portion 203, an intermediate region 205, and a coupling end 206. The forward portion 203 has an external circular cross-sectional area preferably slightly smaller than the internal circular cross-sectional area of the forward position 103 of the leader tube. The intermediate follower region 205 is of the same semi-cylindrical shape as that of the intermediate leader region 105, and the total external cross-sectional area of the two adjacent tubes along the intermediate regions 105, 205 is approximately equal to the external cross-sectional area of the forward leader portion 103. Finally, the coupling end 206 of the follower tube is of the same construction as the leader tube coupling end 106, bent away to form the shape of a "Y". Preferably, the two coupling ends 106, 206 will be bent in such a manner as shown in FIG. 9 that once the cannula 124 is inserted into a body it can lie flat against that body.

The leader tube 101 and follower tube 201 are now easily assembled into a complete dual flow cannula 124. The forward portion 203 of the follower tube is inserted into the forward portion 103 of the leader tube, through the opening 109 next to the shield segment 108. As mentioned above, the forward follower portion 203 is so dimensioned as to fit snugly into the forward leader portion 103. By this arrangement the two tubes 101, 201 will be held together at their forward portions 103, 203. Additional means for holding the two tubes together include medical grade adhesive silicone between the two intermediate regions 105, 205 as with the cannula 24 of the first embodiment shown in FIG. 1. Additionally, the two tubes 101, 201 are secured by a sleeve 113 which is in a tight fitting arrangement about the two tubes. This sleeve 113 may be of the same construction as the sleeve 13 of FIG. 1 described above, or it may include a finger 112 which is bent around the two tubes 101, 201 at the crotch of the "Y". Finally, there is provided a sleeve of Tygon tubing 114, as well as the sections 115, 116, 117, 118 of Tygon tubing which are slid over the coupling ends 106, 206 of the leader and follower tubes (as shown in FIG. 8) and these are of the same construction respectively as the Tygon sleeve 13 and tubing 15, 16, 17, 18 of the cannula 24 of the first embodiment.

The preferred use of the present invention involves the insertion of the cannula into a fistula of a vein. Referring to FIG. 7, such a fistula 20 (or blood bubble) is formed in the vein 21 past the point where an artery 22 and vein 21 are surgically joined via a T-joint connection 23. The cannula 24 should be inserted in the direction of the bloodstream in the vein 21. In this manner the venous tube cannula aperture 30 will be downstream from the arterial tube cannula aperture 9. Furthermore, the cannula 24 should be inserted a distance sufficiently great so that the flap 8 and arterial tube cannula aperture 9 are also located in the fistula 20 of the vein 21.

Blood is withdrawn from the fistula 20 through the arterial tube cannula aperture 9 by means of a pump 25. The flap 8 prevents the walls of the blood vessel from collapsing around and closing off the arterial tube cannula aperture 9. The blood is then pumped through the arterial tube 7 through tubing 15, 17 cemented to the coupling end 12 of the arterial tube and fitted with a Luer adapter 19. The blood is then pumped through tubing to a pillow 26,. This pillow expands and contracts in monitoring the blood pressure. The blood, as withdrawn, can then be studied or treated, as with a kidney dialysis machine 27.

Blood is pumped from the kidney dialysis machine 27 to the bubble trap 28 and screen 29. The blood is then pumped through tubing 16, 18 cemented to the coupling end 6 of the venous tube and fitted with a Luer adapter 19. The blood is returned to the vein 21 on emerging from the venous tube cannula aperture 30. As mentioned above, the blood returning to the body will emerge downstream from the arterial tube cannula aperture 9.

The second embodiment of the cannula 124 of the present invention, as shown in FIG. 8, is used in a manner similar to that of the first embodiment just described. The blood flow through the intake passageway and outflow passageway of the second embodiment is the same as in the first embodiment, but the two tubes 101, 201 form the two passageways in a somewhat different manner. With the cannula 124 sufficiently inserted into a blood vessel, blood is withdrawn through the aperture 109 which is partially shielded by the shield segment 108. Blood is then withdrawn through the intake passageway formed by the intermediate portion 105 of the leader tube, after which the blood flows through the leader tube coupling end 106 to the blood treatment means. After treatment, the blood returns to the body by entering the follower tube coupling end 206, flowing through the complete length of the follower tube and out of the forward follower portion 203, then through the forward leader portion 103, and exiting the cannula through the cannula aperture 130 by the point 102. The forward portion 103 of the leader tube thus serves, together with the follower tube 201, to form the outflow passageway, and forms no part of the intake passageway. It should be emphasized that the two streams of blood, withdrawal and return, are maintained separate at all times within the cannula 124.

Having thus described the principles of the invention, together with several illustrative embodiments thereof, it is to be understood that, although specific terms are employed, they are used in a generic and descriptive sense and not for purposes of limitation, the scope of the invention being set forth in the following claims.

I claim:

1. A cannula for insertion into a blood vessel comprising a first tube having a piercing tip on the forward end thereof and a second tube adjoining said first tube along a region of tangency and having a non-piercing tip on the forward end thereof, said non-piercing tip cooperating with the external wall of said first tube to form aperture means, said first tube having a longitudinal recess along said region of tangency adapted to receive said second tube, said non-piercing tip being turned down and secured to said first tube at one end of and within said longitudinal recess, the cross-section of each of said tubes along said region of tangency being mutually congruent and mutually cooperating to form a cylindrical periphery, the internal cross-sectional area of each of said tubes being a minimum along said region of tangency, whereby said second tube can follow said first tube as the cannula is inserted into a blood vessel of a human or animal body, said aperture means being shielded against blood vessel collapse while still permitting effective withdrawal of blood therethrough, said first and second tubes together forming a substantially continuous, smooth external surface to said blood vessel.

2. The cannula according to claim 1 wherein said first tube and said second tube are held firmly together by nontoxic and nonpyrogenic sealing means along said region of tangency.

3. The cannula according to claim 2 wherein said first and second tubes are additionally held together by a cylindrical sleeve circumscribing both of said tubes along at least a portion of said region of tangency.

4. A cannula comprising a first tube and a second tube forming a forked tubular structure comprising a stem portion, a discharge branch portion and an intake branch portion, said stem portion terminating in a needle with a cannula aperture which is one end of a discharge tubular passageway bounded at least in part by a discharge tube wall and leading to said discharge branch portion but not to said intake branch portion, said stem portion having a substantially unform periphery along its length so as to be adapted for insertion into a blood vessel, said stem portion having a lateral aperture spaced intermediate said needle and said branch portions, said lateral aperture being one end of an intake tubular passageway bounded by an intake tube wall, said intake tubular passageway leading to said intake branch portion but not to said discharge branch portion, wherein said first tube forms said intake tube wall and said intake tubular passageway but also extends beyond said lateral aperture so as to form a forward portion terminating in said apertured needle, and wherein said second tube forms said discharge tube wall and extends in snug fitting arrangement inside said forward portion of said first tube the portion of said intake tube wall which is laterally remote from said discharge tube wall extending beyond the portion of said intake tube wall which is closest to said discharge tube wall and forming with said discharge tube wall a structure which preserves a substantially continuous, smooth external surface to said blood vessel, said extension being so shaped and dimensioned as to shield said lateral aperture against blood vessel collapse while still permitting effective withdrawal of blood through said lateral aperture.

5. A system for the treatment of blood, comprising, in combination with the cannula according to claim 1, pumping means for withdrawal and return of blood through said cannula;

blood treatment means;

and conduit means for transporting blood from the intake tubular passageway of said cannula to the pumping means, to the blood treatment means, and to the discharge tubular passageway of said cannula.

* * * * *